(12) United States Patent
Brugger et al.

(10) Patent No.: US 6,596,260 B1
(45) Date of Patent: *Jul. 22, 2003

(54) AEROSOL CONTAINER AND A METHOD FOR STORAGE AND ADMINISTRATION OF A PREDETERMINED AMOUNT OF A PHARMACEUTICALLY ACTIVE AEROSOL

(75) Inventors: François Brugger, Waltenheim (FR); Angelika Stampf, Rixheim (FR)

(73) Assignee: Novartis Corporation, New York, NY (US)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 08/288,415

(22) Filed: Aug. 10, 1994

(30) Foreign Application Priority Data

Aug. 27, 1993 (EP) ............................................. 93810614

(51) Int. Cl.⁷ ................................................ A61L 9/04
(52) U.S. Cl. .................... 424/45; 128/200.24; 222/635; 239/337
(58) Field of Search ...................... 128/200.24; 424/45; 222/402.24, 635, 402.1, 372, 386, 380; 239/337

(56) References Cited

U.S. PATENT DOCUMENTS

| | | | |
|---|---|---|---|
| 2,815,889 A | | 12/1957 | Stetz et al. |
| 2,886,217 A | | 5/1959 | Thick |
| 3,611,990 A | * | 10/1971 | Paoletti et al. |
| 4,285,937 A | | 8/1981 | Kalvoda |
| 4,762,254 A | | 8/1988 | Nitta |
| 4,902,318 A | | 2/1990 | Stevens et al. |
| 5,149,717 A | | 9/1992 | von Sprecher et al. |
| 5,349,947 A | * | 9/1994 | Newhouse et al. .... 128/203.21 |

FOREIGN PATENT DOCUMENTS

| | | |
|---|---|---|
| DE | 122651 | 10/1966 |
| DE | 1226251 | 10/1966 |
| EP | 0338670 | 10/1989 |
| EP | 0338670 | 10/1998 |
| FR | 2267496 | 11/1975 |
| GB | 2077229 | * 5/1980 |

(List continued on next page.)

OTHER PUBLICATIONS

Parsons et al; International J. Pharmaceutics 83(1992) 163–170 "The Use of Surface Energy and Polarity Determinations . . . ".

(List continued on next page.)

Primary Examiner—Jose' G. Dees
(74) Attorney, Agent, or Firm—John D. Thallemer

(57) ABSTRACT

The invention relates to an aerosol container for pharmaceutically active aerosols that are to be administered in predetermined amounts and that are supplied in the container in the form of a suspension, the suspension also comprising, in addition to a pharmaceutically active substance, at least a propellant gas. The aerosol container has a metering valve that comprises a metering chamber and a valve stem. In a first position of the valve stem, the metering chamber is in communication with the interior of the container and has been filled with a predetermined amount of the aerosol. In a second position of the valve stem, the amount of aerosol disposed in the metering chamber is released. The propellant gas is an alternative propellant gas that is free of fluorochlorohydrocarbons, preferably a propellant gas that comprises only fluorohydrocarbons, and the inner wall of the container is coated with a plastics coating.

14 Claims, 1 Drawing Sheet

FOREIGN PATENT DOCUMENTS

| GB | 2077229 | | 12/1981 |
|---|---|---|---|
| GB | 2216794 A | | 10/1989 |
| GB | 2216794 | | 10/1989 |
| WO | 111190 | * | 7/1992 |
| WO | 921190 | | 7/1992 |
| WO | 9211190 | | 7/1992 |
| WO | 93/11743 | | 6/1993 |

OTHER PUBLICATIONS

Felts; Plasma Deposited Silica Coatings For High Barrier Film and Rigid Containers 1989 149–163.

Derwent Abstract 88–245736/35 of JP 6 3178 038A 1988.

Derwent Abstract 84–280209/45 of JP 5 9174–479–A 1984.

The Aerosol Handbook, pp. 63–64, 175 (1982).

Parsons et al., "The use of surface energy and polarity determinations to predict physical stability of non–polar, non–aqueous suspensions," Int'l J. Pharm. 83 (1992) 163–70.

Derwent Abstract 88–245736/35 of JP 63178038A, 1988.

Derwent Abstract 84–280209/45 of JP 59174–479–A, 1984.

Gennaro, A.R., 1985, Remington Pharmaceutical Sciences, Mack Pub. Co., pp. 1670–1677.

Moren et al., Aerosols in Medicine, 2nd ed., 1993, Elsevier Sci. Pub., Amsterdam, pp. 321–350.

Felts, John T., "Plasma Deposited Silica Coatings For high barrier Film and Rigid Containers," Airco Coating Technology, Concord, CA (1989), pp. 149–163.

Brydson, J.A., Plastics Materials, Ch. 13: "Fluorine Containing Polymers" 4th Ed. Butterworths, London (1982), pp. 332–350.

Morén, F. et al. (1993). Aerosols in Medicine, 2nd ed., Elsevier Sci., Pub., Amsterdam. pp. 321–350.*

Gennaro, A. R. (1985). Remington's Pharmaceutical Sciences., Mack Pub. Co., pp. 1670–1677.*

* cited by examiner

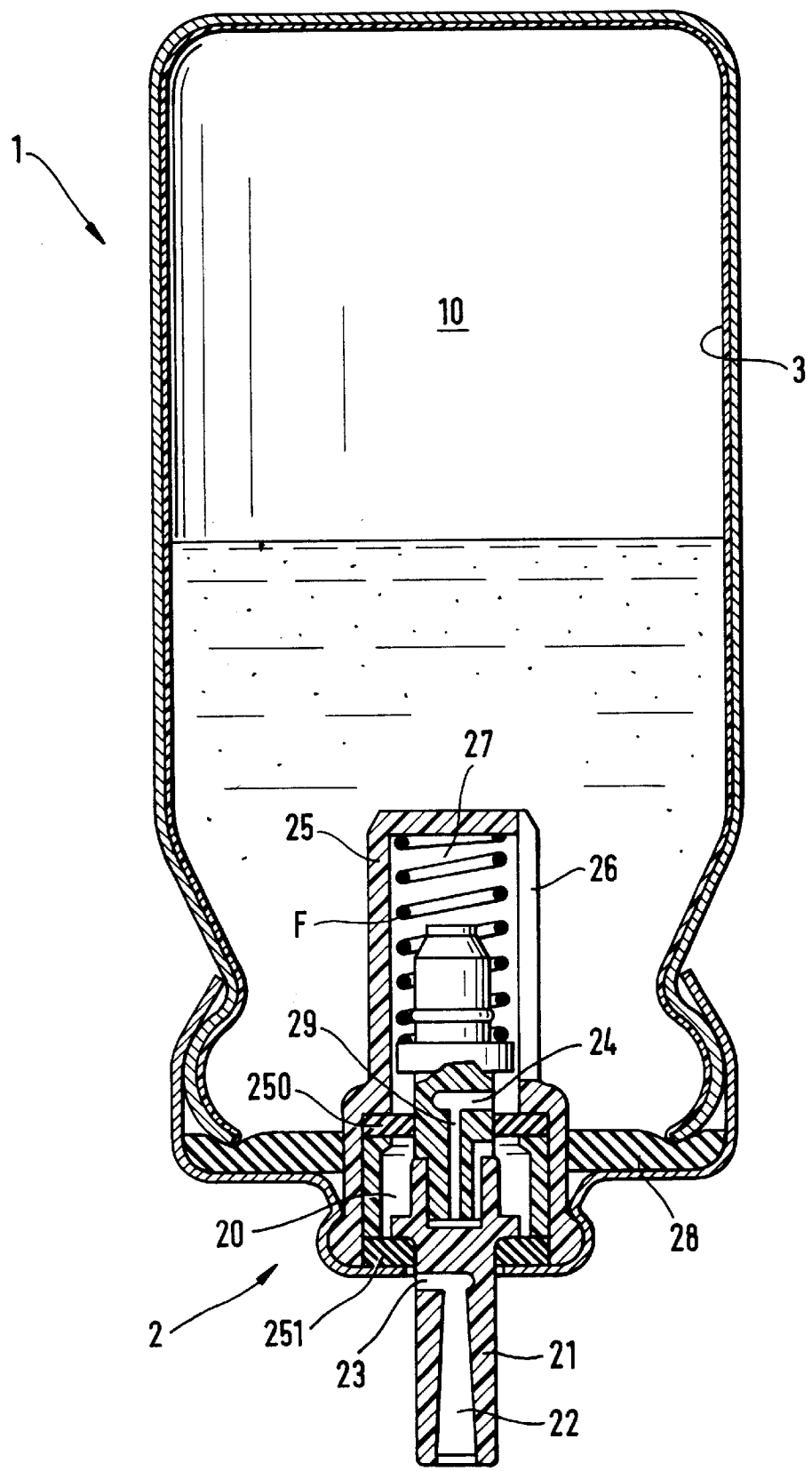

AEROSOL CONTAINER AND A METHOD FOR STORAGE AND ADMINISTRATION OF A PREDETERMINED AMOUNT OF A PHARMACEUTICALLY ACTIVE AEROSOL

BACKGROUND OF THE INVENTION

The invention relates to an aerosol container and to a method for storage and administration of a predetermined amount of a pharmaceutically active aerosol in accordance with the respective independent patent claim.

Aerosols are today a common dosage form for pharmaceutically active substances. Many of those aerosols are to be administered in predetermined (metered) amounts. For various reasons (for example stability), certain pharmaceutically active substances are supplied in the form of a suspension, that is to say the pharmaceutically active substance is present in the aerosol container, usually under pressure, in the form of small solids particles in a liquid, the liquid also comprising at least a propellant gas. That kind of formulation of pharmaceutically active substances has proved suitable for many substances, and especially also for corticosteroids.

In order to administer a predetermined amount of the pharmaceutically active substance, customary aerosol containers are provided with a metering valve having a metering chamber. In a first position of the valve, the metering chamber is in communication with the interior of the container and, in that position, has been filled with the predetermined amount of suspension. In a second position of the metering valve, the amount disposed in the metering chamber is then released in the form of an aerosol, since the liquid/solid mixture can expand. In that manner the aerosol can be administered, for example orally or nasally, to the user.

Hitherto, the propellant gases used have been the widely known fluorochlorohydrocarbons. Those chlorinated propellant gases are now known to be harmful, since they destroy the ozone layer, and they therefore should, and must, be abolished and replaced by other propellant gases that do not damage the ozone layer. In some countries, very recently those propellant gases which comprise chlorinated hydrocarbons have even been banned by law.

So-called "alternative propellant gases" are therefore presented as an alternative, since they do not damage the ozone layer (ozone-depleting potential=0). However, many pharmaceutical substances, when stored in the form of a suspension, are deposited on the inner wall of the container when those propellant gases are used, whereas that did not occur, or occurred only to a very small extent, when chlorinated hydrocarbons were used. Such deposits on the inner wall of the container may result in the desired amount of pharmaceutical active substance that is to be administered to the user not being present in the metering chamber. A further consequence is that the total amount of pharmaceutically active substance stored in the container cannot be administered, since a very considerable proportion of the total amount of pharmaceutically active substance introduced into the container remains deposited on (adheres to) the inner wall of the container.

The aim of the invention is therefore to provide a container in which the pharmaceutically active substance can be supplied in the formulation that has already proved suitable and in which, at the same time, it is possible for alternative propellant gases that do not damage the ozone layer to be used, without significant amounts of the pharmaceutically active substance being deposited on the inner wall of the container. In particular, that is to be possible for anti-asthmatically active pharmaceutical substances (for example corticosteroids), but of course the intention is for it also to be possible for other classes of pharmaceutical substances to be stored in such containers without any significant deposits of active substance being deposited on the inner wall of the container.

SUMMARY OF THE INVENTION

The aim is achieved in accordance with the invention by a container in which the inner wall is coated with a plastics coating and in which the propellant gas is a propellant gas that is free of fluorochlorohydrocarbons, preferably a propellant gas that comprises only fluorohydrocarbons and, where appropriate, also cosolvents and/or surfactants. With such an arrangement, on the one hand no or no significant amounts of active substance are deposited on the inner wall of the container, and on the other hand the ozone layer is not damaged or destroyed. Especially advantageous materials that may be used for the plastics coating are, for example, polytetrafluoroethylene, widely known as Teflon, and also perfluoroethylenepropylene.

BRIEF DESCRIPTION OF THE DRAWING

For a better understanding of the invention, reference is had to the following description taken in connection with the accompanying drawing.

The drawing is a cross-sectional view of an aerosol container constructed in accordance with the invention.

DESCRIPTION OF THE PREFERRED EMBODIMENTS

In specific example embodiments of aerosol containers in accordance with the invention, the thickness of the container wall may be in the range from approximately 0.1 mm to approximately 2 mm, and may be especially approximately 0.4 mm (depending on the material used), and the thickness of the plastics coating may be in the range from approximately 1 nm to approximately 1 mm, and may be especially some 10 nm. The wall thicknesses mentioned are customary for aerosol containers, so that the aerosol containers according to the invention, purely externally and especially in respect of external dimensions, do not differ from customary containers and therefore, even if they have to be used to deliver the aerosol, for example, into an applicator for customary aerosol containers, their use poses no problem.

The volume of the interior of the container of such aerosols is in the range from approximately 1 ml to approximately 100 ml and the volume of the metering chamber is in the range from approximately 5 $\mu$l to approximately 400 $\mu$l. Those volumes are customary, for example, when corticosteroids are used as the pharmaceutically active substance, for example for the corticosteroid with the chemical name "9$\alpha$-chloro-6$\alpha$-fluoro-11$\beta$, 17$\alpha$-dihydroxy-16$\alpha$-methyl-3-oxo-androsta-1,4-diene-17$\beta$-methoxycarbonyl-17-propionate", but also for other pharmaceutically active and, especially, anti-asthmatically active substances, such as, for example, Pormoterol, which may be in the form of its salt, Formoterol fumarate, the name of which according to IUPAC nomenclature is "($\pm$)2'-hydroxy-5-[(RS)-1-hydroxy-2-[[(RS)-p-methoxy-$\alpha$-methylphenethyl]amino]ethyl]formanilide.fumarate.dihydrate", or also for mixtures of Formoterol and the mentioned corticosteroid.

An especially suitable pharmaceutically active substance is the substance called "(1R,2S)-(3E,5Z)-7-[1-(3- trifluoromethylphenyl)-1-hydroxy-10-(4-acetyl-3-hydroxy-2-propylphenoxy)-3,5-decadien-2-ylthio]-4-oxo-4H-1-benzopyrane-2-carboxylic acid" or a sodium salt of that substance, since with those substances especially small deposits, or no deposits at all, occur on the inner wall of the container. The complete aerosol may therefore in that case comprise 0.1% to 2% of that active substance and HFA propellant gases (where appropriate, cosolvents and/or surfactants may also be included).

In the following, the invention is explained in detail with reference to the drawing. The single drawing is a diagrammatic representation in section of an example embodiment of an aerosol container according to the invention. The aerosol container is shown in the drawing in its "in use" position.

The aerosol container is indicated generally by the reference numeral 1. The inner wall of the container 1 is coated with a plastics coating 3, the importance of which will be dealt with in more detail further below. Mounted on the aerosol container 1 is a metering valve 2. The metering valve 2 comprises a valve stem 21, which is guided in a valve housing 25 and is displaceable against the force of a spring F in the valve housing 25. Provided in the wall of the valve housing 25 are individual slots 26 which place the interior 10 of the container 1 in communication with the interior 27 of the valve housing 25. The metering valve 2 also comprises a metering chamber 20, which is filled in a manner explained hereinafter through the slots 26 in the wall of the valve housing 25 with the aid of the valve stem 21. The interior 27 of the valve housing 25 is sealed from the metering chamber 20 by means of a seal 250; the metering chamber 20 is in turn sealed from the outside by a seal 251. Finally, the entire interior 10 of the container is in addition sealed from the outside by means of a seal 28 provided in the metering valve 2.

The stem 21 of the metering valve 2 has two channels 29 and 22. The channel 29 has at its "inner" end a transverse bore 24 which, in the illustrated first position of the stem 21, opens into the interior 27 of the valve housing 25 and thus places the interior 27 of the valve housing, and therefore the interior 10 of the container, in communication with the metering chamber 20. The volume of the metering chamber 20 determines the desired amount of aerosol that is to be administered. How that chamber is filled will be explained later. In any event, in that first position of the stem 21 no aerosol can escape from the metering chamber 20 to the outside, since the metering chamber 20 is sealed from the outside by the seal 251.

In the second position of the valve stem 21, the spring F is compressed and the stem 21 is pushed so far into the interior 27 of the valve housing 25 that there is no communication from the interior 27 of the valve housing 25 and from the interior 10 of the container 1 via the channel 29. In that second position of the stem 21, however, there is communication from the metering chamber 20 out to the user by means of a transverse bore 23 at the "inner" end of the channel 22. The amount of aerosol disposed in the metering chamber 20 can expand through that transverse bore 23 and the channel 22 and thus be administered to the user either directly or by means of a special applicator.

When the valve stem 21 is released again after the administration, the transverse bore 23 passes into the region of the seal 251, and the metering chamber 20 is sealed from the outside again. The stem 21 is at that point not yet back in its first end position, but the transverse bore 24 is already in communication with the interior 10 of the container 1, so that, as a result of the pressure difference (excess pressure in the container interior, discharged metering chamber), suspension immediately flows from the interior 10 of the container into the metering chamber 20 and fills that chamber. The metering chamber 20 is thus immediately refilled when the stem 21 is released or returned and the next administration can therefore follow straightaway.

As has already been mentioned in the introduction, for various reasons (for example stability), many pharmaceutically active substances are supplied in the container under pressure in the form of a suspension, that is to say in the form of a liquid comprising the active substance in the form of solids particles. The liquid also comprises at least a propellant gas so that, in the second position of the stem 21, the metered amount disposed in the metering chamber 20 can expand and can thus be administered to the user directly or by means of a special applicator, as has already been explained above.

Since the propellant gas comprises fluorohydrocarbons (preferably, for example, tetrafluoroethane or heptafluoropropane) and is therefore not harmful to the ozone layer, the inner wall of the container 1 is coated with a plastics coating 3. That plastics coating 3 is preferably of polytetrafluoroethylene, also widely known by the name Teflon, or of perfluoroethylenepropylene, or the layer is produced based on the particular plastics and applied. The use of those materials prevents significant deposits of the active substance on the inner wall of the container 1. The effects of corrosion and electrolysis between the container wall and the liquid or suspension are also avoided.

A wide variety of processes may be used to coat the inner wall of the container 1 with the plastics coating 3. For example, the coating process used may be plasma coating, an impregnating/spraying process, hard anodization with PTFE inclusion, chemical vapour deposition (CVD), physical vapour deposition (PVD) and other processes that are customary for that purpose. The use of plasma coating is especially preferred.

The container wall may be made, for example, from aluminium. The thickness of the wall is, for example, in the range from approximately 0.1 mm to approximately 2 mm and is preferably approximately 0.4 mm. The thickness of the plastics coating is in the range from approximately 1 nm to approximately 1 mm and is preferably approximately some 10 nm to some 10 $\mu$m. Those wall thicknesses are typical of containers that have a total volume in the range from approximately 1 ml to approximately 100 ml and preferably from approximately 5 ml to approximately 20 ml. The metering volume, that is to say the volume of the metering chamber 20, is then, for example, in the range from approximately 5 $\mu$l to approximately 400 $\mu$l and is preferably from approximately 25 $\mu$l to approximately 200 $\mu$l.

The active substance to be administered may be, for example, an anti-asthmatically active substance or substance mixture, especially a substance or substance mixture from the corticosteroid or antiinflammatory steroid classes. Specifically, the corticosteroid may be the corticosteroid with the chemical name "9α-chloro6α-fluoro-11β,17α-dihydroxy16α-methyl-3-oxo-androsta-1, 4-diene-17β-methoxycarbonyl-17-propionate". Equally possible, however, is the administration of other pharmaceutically active and, especially, anti-asthmatically active substances, such as β-sympathomimetics, $LTD_4$ antagonists, parasympatholytics, cromoglycinic acid, or of other active substances that are administered via the lungs, nose or throat, as is the case with some proteins. It is furthermore also possible, for example, to store and administer in that manner Formoterol, for example in the form of its salt, Formoterol fumarate, the name of which according to IUPAC nomenclature is "(±)2'-hydroxy-5'-[(RS)-1-hydroxy-2-[[(RS)-p-methoxy-α-methylphenethyl]amino]ethyl]formanilide.fumarate.dihydrate", or a mixture of Formoterol and the mentioned corticosteroid.

An especially suitable pharmaceutically active substance is also the substance called "(1R,2S)-(3E,5Z)-7-[1-(3-trifluoromethylphenyl)-1-hydroxy-10-(4-acetyl-3-hydroxy-2-propylphenoxy)-3,5-decadien-2-ylthio]-4-oxo-4H-1-b acid", or a sodium salt of that substance, since with those substances especially small deposits, or no deposits at all, occur on the inner wall of the container. The complete aerosol may therefore in that case comprise 0.1% to 2% of that active substance and HFA propellant gases (where appropriate, cosolvents and/or surfactants may also be included).

What is claimed is:

1. An aerosol container system for metering and administering pharmaceutically active aerosols supplied in the form of a suspension, the suspension including a pharmaceutically active agent and a propellant gas free of fluorochlorohydrocarbons, said aerosol container system comprising:

a container for storing the suspension comprising a container wall, the inner portion of said container wall which defines the interior of the container being coated with a plastics coating which inhibits the pharmaceutically active agent in the suspension from depositing thereon, and a metering valve system for dosing and releasing the suspension comprising a metering chamber and a valve stem, said valve stem capable of being displaced from a first position to a second position, wherein in the first position the valve stem affords communication between the interior of the container and the metering chamber while simultaneously blocking communication between the metering chamber and the outside of the aerosol container system such that the metering chamber can be filled with a dose of the suspension from the container, and wherein in the second position the valve stem blocks communication between the interior of the container and the metering chamber while simultaneously affording communication between the metering chamber and the outside of the aerosol container system such that the dose of suspension in the metering chamber can be released from the aerosol container system.

2. An aerosol container system according to claim 1, wherein the plastics coating is polytetrafluoroethylen or perfluoroethylenepropylene.

3. An aerosol container system according to claim 1, wherein the thickness of the container wall is in the range from approximately 0.1 mm to approximately 2 mm, and the thickness of the plastics coating is in the range from approximately 1 mm to approximately 1 mm.

4. An aerosol container system according to claim 1, wherein the volume of the interior of the container is in the range from approximately 1 ml to approximately 100 ml and the volume of the metering chamber is from approximately 5 μl to approximately 400 μl.

5. Method for the storage and administration of a pharmaceutically active aerosol in the form of a suspension, the suspension including a pharmaceutically active agent and a propellant gas that is free of fluorochlorohydrocarbons, wherein a container system according to claim 1 is used.

6. Method according to claim 5, wherein the pharmaceutically active agent in the suspension is an anti-asthmatically active agent.

7. Method according to claim 6, wherein the anti-asthmatically active agent is selected from the group consisting of formoterol, formoterol fumarate, and corticosteroids.

8. Method according to claim 6, wherein the anti-asthmatically active agent is (1R,2S)-(3E,5Z)-7-[1-(3-trifluoromethylphenyl)-1-hydroxy-10-(4-acetyl-3-hydroxy-2-propylphenoxy)-3,5-decadien-2-ylthio]-4-oxo-4H-1benzopyrane-2-carboxylic acid or the sodium salt thereof.

9. An aerosol container system according to claim 1, wherein the propellant gas consists essentially of a fluorohydrocarbons.

10. An aerosol container system according to claim 1, wherein the suspension further includes cosolvents and/or surfactants.

11. An aerosol container system according to claim 3, wherein the thickness of the container wall is approximately 0.4 mm and the thickness of the plastics coating is approximately 10 nm.

12. Method according to claim 5, wherein the propellant gas consists essentially of fluorohydrocarbons.

13. Method according to claim 5, wherein the suspension further includes cosolvents and/or surfactants.

14. Method according to claim 7, wherein the anti-asthmatically active agent includes the corticosteroid 9α-chloro-6α-fluoro-11β, 17α-dihydroxy-16α-methyl-3-oxo-androsta-1,4-diene-17β-methoxycarbonyl-17-propionate.

* * * * *

UNITED STATES PATENT AND TRADEMARK OFFICE
CERTIFICATE OF CORRECTION

PATENT NO.      : 6,596,260 B1                                              Page 1 of 1
DATED           : July 22, 2003
INVENTOR(S)     : Brugger et al.

It is certified that error appears in the above-identified patent and that said Letters Patent is hereby corrected as shown below:

Column 2,
Line 60, "Pormoterol" should read -- Formoterol --.

Column 6,
Line 2, "polytetrafluoroethylen" should read -- polytetrafluoroethylene --.
Line 8, "1 mm to approximately 1 mm." should read -- 1 nm to approximately 1 mm." --.
Line 32, "of a fluorohydrocarbons" should read -- of fluorohydrocarbons --.

Signed and Sealed this

Fourteenth Day of October, 2003

JAMES E. ROGAN
*Director of the United States Patent and Trademark Office*